(12) United States Patent
Laddha

(10) Patent No.: US 11,154,583 B2
(45) Date of Patent: Oct. 26, 2021

(54) COMPOSITION AND METHOD OF SKIN RELIEF CREAM USEFUL FOR ECZEMA, PSORIASIS, LIPOMA, BURN WOUNDS, SCARS, KELOIDS, SHINGLES, DRY SKIN DISORDERS, AND SKIN ALLERGIES

(71) Applicant: Unmesh Dwarkanath Laddha, Marietta, GA (US)

(72) Inventor: Unmesh Dwarkanath Laddha, Marietta, GA (US)

( * ) Notice: Subject to any disclaimer, the term of this patent is extended or adjusted under 35 U.S.C. 154(b) by 60 days.

(21) Appl. No.: 16/658,875

(22) Filed: Oct. 21, 2019

(65) Prior Publication Data

US 2020/0061144 A1    Feb. 27, 2020

Related U.S. Application Data

(60) Provisional application No. 62/748,781, filed on Oct. 22, 2018.

(51) Int. Cl.

| | | |
|---|---|---|
| *A61K 36/00* | (2006.01) |
| *A61K 36/81* | (2006.01) |
| *A61P 17/08* | (2006.01) |
| *A61K 36/38* | (2006.01) |
| *A61K 36/47* | (2006.01) |
| *A61K 36/886* | (2006.01) |
| *A61K 36/9066* | (2006.01) |
| *A61K 31/60* | (2006.01) |
| *A61K 31/5415* | (2006.01) |
| *A61K 8/9789* | (2017.01) |
| *A61K 9/06* | (2006.01) |
| *A61K 9/00* | (2006.01) |
| *A61P 17/06* | (2006.01) |
| *A61P 17/02* | (2006.01) |
| *A61P 17/04* | (2006.01) |
| *A61K 36/8945* | (2006.01) |

(52) U.S. Cl.
CPC ............ *A61K 36/81* (2013.01); *A61K 8/9789* (2017.08); *A61K 9/0014* (2013.01); *A61K 9/06* (2013.01); *A61K 31/5415* (2013.01); *A61K 31/60* (2013.01); *A61K 36/38* (2013.01); *A61K 36/47* (2013.01); *A61K 36/886* (2013.01); *A61K 36/8945* (2013.01); *A61K 36/9066* (2013.01); *A61P 17/02* (2018.01); *A61P 17/04* (2018.01); *A61P 17/06* (2018.01); *A61P 17/08* (2018.01)

(58) Field of Classification Search
None
See application file for complete search history.

*Primary Examiner* — Qiuwen Mi
(74) *Attorney, Agent, or Firm* — Examiner Edge; Gary O'Neill

(57) ABSTRACT

The present invention relates generally to a herbal cream formulation useful for treatment of skin diseases and disorders, therapeutic and cosmetic applications. More specifically, the present invention relates to the composition of a topical cream useful for treating Eczema, Psoriasis, burn wounds, scars, keloids, Lipomas, Shingles, dry skin disorders, skin allergies and other related skin diseases. The present invention includes the composition and method of making the topical cream.

7 Claims, No Drawings

COMPOSITION AND METHOD OF SKIN RELIEF CREAM USEFUL FOR ECZEMA, PSORIASIS, LIPOMA, BURN WOUNDS, SCARS, KELOIDS, SHINGLES, DRY SKIN DISORDERS, AND SKIN ALLERGIES

BACKGROUND OF THE INVENTION

Human skin acts as a barrier between the interior body and exterior environment maintaining a controlled dynamic equilibrium. Stresses imposed by the environment and various human factors such as exposure to sunlight, genetics, eating habits, lifestyle, etc., can cause undesired changes in the skin, thus incurring a skin disease or disorder. Major purpose of cream under consideration is to help reverse these changes and maintain healthy, normal skin. Generally, the most common skin diseases and disorders include Eczema, Psoriasis, burn wounds, Shingles, scaring of skin to form keloids, discoloration or Vitiligo, Lipoma, dry skin, skin allergies, contact dermatitis and cracked heels, etc. These are observed in individuals at various ages.

Eczema is a prevalent skin disorder, encompassing a variety of diseases such as contact dermatitis and dyshidrotic. Eczema is characterized by initial symptoms of blistering and dry cracked skin on the hands or feet, affecting the tips and sides of fingers, toes, soles and palms. The disease develops progressively into continual scaling, peeling, cracked skin, bleeding, deep fissures and open wounds. These conditions cause the skin to become red, itchy and inflamed. There are several types of eczema: atopic dermatitis, contact dermatitis, dyshidrotic eczema, nummular eczema, seborrheic dermatitis and stasis dermatitis. Living with eczema can be an ongoing challenge. It is most common for babies and children to develop eczema on their face (especially the cheeks and chin), but it can appear anywhere on the body. Usually eczema goes away as a child grows older, though some children will continue to experience eczema into adulthood. Adults can develop eczema, too, even if they never had it as a child. Eczema is usually itchy and might develop extremely inflamed skin. The most common treatment includes Eczema phototherapy or light therapy, an eczema treatment that uses ultraviolet light to reduce skin inflammation. The biggest drawback of eczema light therapy is that it is very time consuming and requires many trips to the doctor's office over several weeks. Although there are light therapy units available by prescription to use at home, most dermatologists prefer treatments done in the office where UV light exposure can be controlled. Additionally, the Eczema light therapy may cause burning, headache and nausea, skin damage, and even skin cancer. Another common treatment is prescription topical medication and/or over-the-counter (OTC) remedies, for instance, the use of Cortisone steroid creams. This type of treatment is easy to use, works fast, and costs less than many other treatments. However, the steroid cream treatment normally reduces the symptoms such as itchiness temporarily. As soon the treatment stops, Eczema may come back and becomes even worse than before the treatment. Further, this type of treatment may cause addition and tolerance to the steroid chemicals, and side effects such as skin thinning and degrading, bruising, toxin build-up in the body, and hormone suppression, etc.

Psoriasis is a common skin condition that speeds up the life cycle of skin cells. It causes cells to build up rapidly on the surface of the skin. The extra skin cells form scales and red patches that are itchy and sometimes painful. Psoriasis is a chronic disease that often comes and goes. The main goal of treatment is to stop the skin cells from growing so quickly. Psoriasis signs and symptoms are different for everyone. Common signs and symptoms include:

Red patches of skin covered with thick, silvery scales
Small scaling spots (commonly seen in children)
Dry, cracked skin that may bleed
Itching, burning or soreness
Thickened, pitted or ridged nails
Swollen and stiff joints Psoriasis patches can range from a few spots of dandruff-like scaling to major eruptions that cover large areas. Most types of psoriasis go through cycles, flaring for a few weeks or months, then subsiding for a time or even going into complete remission.

Herpes Zoster, also called Shingles or Acute Posterior Ganglionitis, is infection that results when varicella-zoster virus reactivates from its latent state in a posterior dorsal root ganglion. Symptoms usually begin with pain along the affected site, followed by a rash, usually crop of vesicles on an erythematous base and forming small blisters filled with a serous exudate, as the fever and general malaise continue. The painful vesicles eventually become cloudy or darkened as they are filled with blood, and crust over within seven to ten days; usually the crusts fall off and the skin heals, but sometimes, after severe blistering, scarring and discolored skin remain. The rash is accompanied by severe pain, which, in some people, does not subside after healing but persists for months or years. This prolonged zoster associated pain, usually defined as pain persisting for more than four months after the rash has healed, is known as postherpetic neuralgia and is the most common complication of herpes zoster. The pain can be debilitating, exacerbated by the slightest touch, and lead to loss of employment, depression, and social isolation. There is no cure for Shingles, but prompt treatment with prescription antiviral drugs can speed healing and reduce the risk of complications. However, many antiviral medications can cause side effects such as nausea, headache, rash, diarrhea, etc.

Burn wounds: The skin's three anatomic layers, i.e., epidermis, dermis, and subcutaneous tissue, have functions that are lost after burn injuries. The epidermis is a barrier to bacteria and moisture loss. After a burn injury, local wound care and fluid management are required. The dermis provides elasticity and protection from mechanical trauma, and it contains blood vessels that supply all skin layers. When the skin is damaged, epidermal cells regenerate from cells deep within the dermal appendages, which is why deep dermal injury causes significant scarring and permanent skin damage. Most patients with burn wounds are treated in the outpatient setting, making primary care physicians the main treatment source for thousands of burn patients each year. Superficial (first-degree) burns involve only the epidermis; like a sunburn, they are erythematous, painful, and dry. They are most often the result of severe ultraviolet exposure or minor thermal injury. The most common treatment for skin burns is using creams or lotions such as aloe vera gel, calendula tincture, honey, etc. Many of these creams or lotions have problems that affect the effectiveness, including too little effective ingredient in the formulation, color and/or cosmetic additives, etc.

Lipoma: Lipoma is a benign growth of fatty tissue that slowly develops under the skin. Lipomatous tumors are a common group of mesenchymal lesions. The lipoma is only painful if it grows into nerves underneath the skin. Usually lipomas are not painful, but sometimes can have extra blood vessels mixed in that can be associated with some pain or tenderness. Some lipomas grow noticeably causing concerns. Dermatologist can treat the lump if it bothers the patient. The most common way to treat a lipoma is to remove it through surgery. This is especially helpful if the patient has a large skin tumor that is still growing. However, surgery brings the risk of recurrence, pain, scar, tiny nerve injuries, infection, etc.

Keloids: Keloids are incredibly common in some patient populations. These abnormal scars, which grow well beyond the border of the original injury site, are typically unsightly, inconvenient, and often uncomfortable. Keloids cause pain, pruritic, and even hyperesthesia, as well as social discomfort and embarrassment. Until recently, very little was known about the etiology of keloids, and even less was known about how to effectively treat and manage their growths. Surgical excision is frequently inadequate, because many, if not most, keloids recur after excision. Other treatment measures, including corticosteroid injection and the use of pressure dressings, were based on medical intuition and anecdotal evidence more than scientific research.

The objective of the present invention is to provide relief during these skin problems and obviates the drawbacks of the existing formulations and treatment methods for skin diseases and disorders. More specifically, the present invention provides a natural herbal formulation for therapeutic and cosmetic applications in conditions such as Psoriasis, Eczema affected skin, dry skin disorders, Lipoma, skin allergies, depigmentation or Vitiligo and anti-fungal activity, etc. The preferred embodiment of the formulation of the present invention includes castor seed oil, kokum seed extract, *solanum nigrum* (black nightshade) extract, Aloe Vera, Air Potato Extract and emulsifying agent. Since most of the active ingredients used in the formulation are from herbal sources, the present invention is a safe and eco-friendly treatment, thus, does not produce any harmful effects on the human skin. The present invention can be used alone or in combination with oral folic acid supplements. Further, the present invention is lethal to fungus, mold, bacteria, and yeasts, thus, providing effective treatment of Psoriasis, eczema, burns, keloids, lipoma, scars, contact dermatitis, Shingles and dermatophyte fungi. Another objective of the present invention is to provide a method for preparing an herbal cream using the formulation of the present invention.

SUMMARY OF THE INVENTION

The herbal formulation of the present invention provides a solution of the problems related to the existing formulations and treatment methods for skin diseases and disorders. The formulation can be used for therapeutic and cosmetic applications use such as Eczema and Psoriasis affected skin relief, dry skin disorders, skin allergies, Lipoma, depigmentation and anti-fungal activity, etc. Specifically, the formulation of the present invention includes Castor seed oil, Kokum seed extract, *Solanum Nigrum* (black nightshade) extract, *Dioscorea bulbifera* Linn (Air Potato) extract, Aloe Vera and emulsifying agent. Additionally, most of the active ingredients used in the formulation are from herbal sources. Thus, the present invention offers a safe and eco-friendly treatment, and does not produce any harmful effects on the human skin. The present invention can be used alone or in combination with oral folic acid supplements. Further, the present invention is lethal to fungus, mold, bacteria, and yeasts, thus, providing an effective treatment of lipoma, burns, keloids, scars, contact dermatitis, eczema, Shingles, dermatophyte fungi and skin psoriasis. The present invention further provides a method for preparing an herbal cream using the formulation of the present invention.

BRIEF DESCRIPTION OF DRAWINGS

| Table I | Detail Description of Ingredients |
|---|---|
| Table II | Method of Preparation of the Composition |

DETAIL DESCRIPTION OF THE INVENTION

All illustrations of the drawings are for the purpose of describing selected versions of the present invention and are not intended to limit the scope of the present invention.

The present invention provides a herbal formulation for the treatment and relief of skin diseases and disorders including Psoriasis, Eczema, burn wounds, Shingles, scaring of skin to form keloids, Lipoma, dry skin, skin allergies, contact dermatitis and cracked heels, etc. More specifically, the preferred embodiment of the formulation of the present invention comprises castor seed oil, kokum seed extract, *solanum nigrum* (black nightshade) extract, Aloe Vera, Air Potato Extract and emulsifying agent. As can be seen in TABLE I, the Castor Seed, also known as *Ricinus Communis*, is in oil form and of 2-20% by weight in the formulation. The *Solanum Nigrum* extract can be oil and/or powder or pulp, is of 2-75% by weight. The extract of Kokum Seed, also known as Garcinia Indica, is in the form of oil and of 2-10% by weight. The extract of Air Potato also known as *Dioscorea bulbifera* Linn can be a powder or pulp, is of 2-6% by weight. The emulsification agent is no more than 0.01% by weight in the formulation. The content of Aloe Vera is no more than 8% by weight.

TABLE I

| Ingredients | |
|---|---|
| Ingredient | % By Weight |
| Castor seed oil | 2%-20% |
| Solanum nigrum | 2%-75% |
| Kokum seed oil | 2%-10% |
| Air Potato Extract | 2%-6% |
| Emulsifying agent | ≤0.01% |
| *Aloe vera* | ≤8% |

The preferred embodiment of the formulation of the present invention, as seen in TABLE I, includes extracts and/or oils from medicinal plants thereof having anti-inflammatory, anti-tumor, anti-cancer, antimicrobial, antioxidant, antihistaminic and wound healing properties. Thus, the present invention offers a safe and eco-friendly treatment and does not produce any harmful effects on the human skin. The plant extracts of *Ricinus Communis* (Castor Seed Oil), *Solanum Nigrum* (Black Nightshade), *Dioscorea bulbifera* Linn (Air Potato), Aloe Vera and Garcinia Indica (Kokum Seed) used in the present invention may be from any part of the plant including, but not limited to, leaf, root, bark, exudation of the bark, flower, seed, fruit, stem, and branch.

In another embodiment of the present invention, the formulation may comprise Salicylic acid, Piroxicam, Diclofenac sodium, or any combination thereof in addition to the formulation listed in TABLE I. This embodiment of formulation further enhances the anti-inflammatory and wound healing functions of the present invention.

In still another embodiment of the present invention, the formulation may comprise an aqueous cream base including, but not limited to, emulsifying ointment BP 1993, preservative, and water. The formulation may comprise a gel base including, but not limited to, propylene glycol, Carbopol 934, and mono-ethanol amine, or any combination thereof.

The present invention can be used alone or in combination with oral folic acid supplements. Further, the present invention is lethal to fungus, mold, bacteria, and yeasts, thus, providing an effective treatment of eczema, skin psoriasis, burns, keloids, scars, lipoma, contact dermatitis, Shingles and dermatophyte fungi.

The present invention further comprises a method for preparing an herbal cream or gel using any of the embodiments of the formulation of the present invention described above. The first step in the preparation of these formulations involves a process of making the plant extract of the *Solanum Nigrum* and *Dioscorea bulbifera* Linn suitable for incorporating into a cream or gel base. The appropriate portion of the plants are collected and dried in sunlight for at least 72 hours or until the material is dry. A specific amount of the *Solanum Nigrum* and *Dioscorea bulbifera* Linn material is then extracted with a solvent including, but not limited to, water-hexane, chloroform, ethanol, methanol, and water. The choice of solvent depends upon the type of material expected at the end of the extraction process. The extraction process and creation of the cream of the present invention is described in detail in TABLE II.

The formulations and method of the present invention are based on pharmacological scientific principles rather than literature describing common herbs that are good for the skin. While there are a number of herbal creams on the worldwide market available for the treatment of skin disorders, few contain the active ingredients as described in this invention. Moreover, it has been reported that many marketed herbal topical skin products, either don't work or they are misleading, claiming to be natural, but adulterated with potent steroids.

Because of the intensive study conducted by the inventors with the aim of achieving aforementioned objectives, new processes for the preparation of cream formulations for topical use were developed employing herbal drugs which are from natural origin, incorporating them into cream bases along with synthetic materials which are known to possess water retaining properties. Thus, the present invention provides an effective treatment of skin relief for psoriasis, eczema, burns, keloids, scars, contact dermatitis, lipoma, Shingles and dermatophyte fungi and an efficient method of making the formulations.

Although the invention has been explained in relation to its preferred embodiment, it is to be understood that many other possible modifications and variations can be made without departing from the spirit and scope of the invention.

TABLE II

| No. | Step | Sub Step |
| --- | --- | --- |
| | Method of Preparation | |
| 1. | Preparation of decoction | 1. Take a specific amount of *Solanum nigrum* (leaf, root, stem, flower, fruits, etc.) after at least 72 hours of drying in direct Sunlight.<br>2. Add specific amount of Air Potato Extract (leaf, root, stem, flower, fruits, etc.) after at least 72 hours of drying in direct Sunlight.<br>3. Prepare pulp using a mixer grinder.<br>4. Add eight times of water by weight to the mixer.<br>5. Heat the mixture to 30-50° C. to reduce the mixture to 50% by weight.<br>6. Filter and collect filtrate in a stainless-steel pot. |
| 2. | Preparation of *Solanum nigrum* and *Dioscorea bulbifera* Linn oil | 1. Take one part of pulp prepared in step 1 in a stainless-steel pot.<br>2. Add four parts of Castor oil to the pot.<br>3. Add 2 parts of *Aloe Vera* to the pot.<br>4. Add 16 parts of the decoction prepared in Step 1 to the pot.<br>5. Heat the mixture to 100-120° C. to dry the mixture to no more than 5% moisture by weight.<br>6. Filter and collect filtrate in a stainless-steel pot. |
| 3. | Preparation of cream | 1. Take 2 kg of the *Solanum nigrum* and *Dioscorea bulbifera* Linn oil prepared in Step 3 in a homogenizer.<br>2. Heat 1 kg of Kokum seed to 70-80° C. to melt in a stainless-steel pot.<br>3. Add the melted Kokum seed to the homogenizer.<br>4. Add emulsifying agent of no more than 0.01% by weight to the mixture.<br>5. Homogenize the mixture to make a cream.<br>6. Collect the cream in a stainless-steel pot. |
| 4. | Storage | 1. Store the resulted cream in cool, dry place. |

The above formulation listed in Table II was tested for multiple cases of Psoriasis, Eczema, Lipoma, Shingles, Burn Wounds, Keloids and Scars for relief on human subjects of both sexes of different age groups in India during a period of 2 years.

The skin cracks in all cases were healed within 1 to 2 weeks when applied twice daily. Moderate skin problems and wounds were healed within 7 days and severe skin cracks were healed by continuous use of 1 to 2 months in case of Psoriasis and Eczema. The natural suppleness of the skin was restored in all cases after healing. Few subjects reported healing of even leprosy wounds on hands, fingers and toes. Several subjects with severe case of Psoriasis reported total healing of skin on both hands after continuous use of 1 to 2 months. Multiple cases also reported immediate relief from Shingles pain. In all the subjects, soothing effect was observed after one or two applications and new rejuvenated skin was formed in matter of days.

The above observations ascertain that formulation described in Table II above is best for various types of skin diseases, rash, skin allergies and other skin problems in all cases.

The main advantages of the present invention are:
1. It spreads evenly on the applied parts and after a light massage, gets absorbed in the skin. After application, the skin has an immediate softening and soothing effect.
2. It heals the skin cracks and wounds rapidly and makes the skin soft and supple in all observed cases.
3. The formulation also acts as an antiseptic in case of wounds from Eczema, Psoriasis, Burn Wounds, cuts and rashes. It is observed that the formulation stops the skin scaling, minimizes skin fissures, red rashes and pain and helps grow new skin quickly in cases of Eczema, Psoriasis, burn wounds and severe itching.
4. The formulation is an emollient cream which prevents water loss from the skin cracks and promotes healing in cases of Eczema, Psoriasis and Burn wounds. It also has antifungal activity and hence can be used for fungal infections on skin.
5. The present formulations, apart from healing the cracks on skin, are useful in arresting the bleeding due to cracks and reducing the pain as well as give soothing relief in most cases.
6. Once the cracks on skin are cured, the recurrence of cracks is minimum, compared to commercially available products in the market.
7. The present formulation has moisturizing effect on skin and hence can be used for any dry skin disorders in cosmetic therapy.
8. The present formulation provides excellent protection from darkening of skin due to minor cuts, burns, wounds and pimples.
9. The present formulation has good antiallergic activity in case of insect bites, rashes and reduce itching on the skin.
10. The present formulations can also be used as base material in which ingredients have analgesic, anticancer, antioxidant and anti-inflammatory properties which can be incorporated for potentiation of their activities.

What is claimed is:

1. A composition in the form of a cream for therapeutic and cosmetic treatment of general skin disorders including Psoriasis, Eczema, burn wounds, Shingles, dispigmentation, discoloration, Vitiligo, dry skin, Keloids, scars, lipoma, allergic rashes and irritation, fungal infections, said composition comprising:
(a) A plurality of plant extracts formed as an oil, a powder, or mixtures thereof, the plant extracts including:
*Solanum Nigrum* water extract in 2 to 75 wt. %, said *Solanum Nigrum* having been dried for at least 72 hours in direct sunlight; *Dioscorea bulbifera* Linn water extract in 2 to 6 wt. %, said *Dioscorea bulbifera* Linn having been dried for at least 72 hours in direct sunlight; the mixture of the plurality of plant extracts having been heated to 30 to 50 degrees C.; and Garcinia Indica extract in 2 to 10 wt. %; *Ricinus Communis* oil extract in 2 to 20 wt. %; juice of Aloe Vera in 2 to 8 wt. %; Polyoxyethylene (20) sorbitan monooleate emulsifying agent in 0.005 wt. % to 0.01 wt. %; fragrant oil selected from the group consisting of Rose, Basil, Chamomile oil and Mentha oil in 0.005 wt. % to 0.01 wt. %;
(b) further comprising a drug having anti-inflammatory and wound healing properties selected from the group consisting of Salicylic acid in 1 to 4 wt. %, Piroxicam in 1 to 2 wt. %, Turmeric Powder in 0.1 to 1 wt. % and mixtures thereof;
(c) and a first base or a second base, said first base comprising propylene glycol, cross-linked polyacrylic acid polymer, mono-ethanol amine and petroleum jelly in 2 to 20 parts by weight or mixtures thereof; and said second base comprising an aqueous cream base or gel containing cross-linked polyacrylic acid polymer in 1 to 4 wt. %, water in 20 to 40 wt. %, and a humectant in 1 to 4 wt. %.

2. The composition as claimed in claim 1 wherein the humectant is glycerin and ranges between 1 to 4 wt. %.

3. The composition as claimed in claim 1 wherein the humectant is propylene glycol in 1 to 3 wt. %.

4. The composition as claimed in claim 1 useful in enhancing the healing of skin during Psoriasis, Eczema, Burn Wounds, Scars, Lipoma, Shingles, discoloration, dry skin disorders, fungal infections and skin allergies with minimum recurrences.

5. The composition as claimed in claim 1 which can be used alone or in combination with oral folic acid supplements.

6. The composition as claimed in claim 1 which is lethal to fungus, mold, bacteria, and yeasts, thus providing an effective treatment of Psoriasis, Eczema, burns, keloids, scars, contact dermatitis, shingles and dermatophyte fungi.

7. The composition as claimed in claim 1, wherein said composition provides a synergistic effect which enables said composition to quicken healing when applied to cracked skin.

* * * * *